(12) United States Patent
Lalonde

(10) Patent No.: US 9,925,359 B2
(45) Date of Patent: Mar. 27, 2018

(54) BALLOON DESIGN TO REDUCE DISTAL LENGTH

(71) Applicant: Medtronic CryoCath LP, Toronto (CA)

(72) Inventor: Jean-Pierre Lalonde, Candiac (CA)

(73) Assignee: Medtronic CryoCath LP, Toronto, Ontario (CA)

( * ) Notice: Subject to any disclaimer, the term of this patent is extended or adjusted under 35 U.S.C. 154(b) by 444 days.

(21) Appl. No.: 14/221,763

(22) Filed: Mar. 21, 2014

(65) Prior Publication Data

US 2015/0265812 A1  Sep. 24, 2015

(51) Int. Cl.
*A61B 18/02* (2006.01)
*A61M 25/10* (2013.01)
(Continued)

(52) U.S. Cl.
CPC ......... *A61M 25/1011* (2013.01); *A61B 18/02* (2013.01); *A61B 18/1492* (2013.01);
(Continued)

(58) Field of Classification Search
CPC .............. A61B 18/02; A61B 18/00577; A61B 18/0212; A61B 18/1492;
(Continued)

(56) References Cited

U.S. PATENT DOCUMENTS 3,833,004 A    9/1974  Vazquez et al.
4,315,512 A *  2/1982  Fogarty ............... A61M 25/104
                                                       604/103.11

(Continued)

FOREIGN PATENT DOCUMENTS

CA    2666334 A1    3/2003
CA    2804690 A1    2/2012
(Continued)

OTHER PUBLICATIONS

International Search Report and Written Opinion dated Jun. 10, 2015 for International Application Serial No. PCT/CA2015/000167, International Filing Date: Mar. 18, 2015, consisting of 10 pages.
(Continued)

*Primary Examiner* — Michael Peffley
*Assistant Examiner* — Khadijeh Vahdat
(74) *Attorney, Agent, or Firm* — Christopher & Weisberg, P.A.

(57) ABSTRACT

A device and system for thermally affecting tissue that includes a balloon catheter with a reduced distal length for ease of navigation and that also includes a balloon that is more resistant to bursting and delamination. The balloon may include a proximal neck generally attached to an elongate body and a distal neck generally attached to a shaft disposed within the elongate body. The distal neck is turned inward to extend within the balloon chamber and the proximal neck may either extend within the chamber or extend proximally away from the balloon chamber. Alternatively, the device may include an inner balloon and an outer balloon, the distal necks of both being turned inward and extending within the inner balloon chamber. The proximal necks may both also be turned inward to extend within the chamber or the proximal neck of the outer balloon may extend away from the balloon chamber.

10 Claims, 6 Drawing Sheets

(51) Int. Cl.
*A61B 18/14* (2006.01)
*A61B 18/00* (2006.01)

(52) U.S. Cl.
CPC ............ *A61B 2018/0025* (2013.01); *A61B 2018/00357* (2013.01); *A61B 2018/00577* (2013.01); *A61B 2018/0212* (2013.01); *A61M 2025/1013* (2013.01)

(58) Field of Classification Search
CPC .... A61B 2018/0022; A61B 2018/0025; A61B 2018/00255; A61B 2018/00357; A61B 2018/00375; A61B 2018/0262; A61M 25/1011; A61M 25/1013
USPC ................................ 604/101.02; 606/21–26
See application file for complete search history.

(56) References Cited

U.S. PATENT DOCUMENTS

| | | | |
|---|---|---|---|
| 5,108,370 A | 4/1992 | Walinsky | |
| 5,571,088 A * | 11/1996 | Lennox | A61B 8/12 604/96.01 |
| 5,766,151 A * | 6/1998 | Valley | A61B 17/00234 604/103.07 |
| 5,868,735 A * | 2/1999 | Lafontaine | A61B 18/02 606/21 |
| 5,997,503 A | 12/1999 | Willis et al. | |
| 6,053,913 A | 4/2000 | Tu et al. | |
| 6,117,101 A | 9/2000 | Diederich et al. | |
| 6,186,978 B1 * | 2/2001 | Samson | A61M 25/005 604/525 |
| 6,254,570 B1 | 7/2001 | Rutner et al. | |
| 6,432,080 B2 | 8/2002 | Pederson, Jr. et al. | |
| 6,468,268 B1 | 10/2002 | Abboud et al. | |
| 6,679,861 B2 | 1/2004 | Yozu et al. | |
| 6,942,640 B2 | 9/2005 | Kokish | |
| 7,708,716 B2 | 5/2010 | Shah | |
| 7,744,594 B2 | 6/2010 | Yamazaki et al. | |
| 7,780,628 B1 | 8/2010 | Keren et al. | |
| 8,460,240 B2 | 6/2013 | Towler | |
| 9,387,031 B2 * | 7/2016 | Stewart | A61B 18/02 |
| 2005/0015047 A1 * | 1/2005 | Shah | A61M 25/1011 604/101.02 |
| 2005/0203597 A1 * | 9/2005 | Yamazaki | A61B 18/1492 607/98 |
| 2010/0241070 A1 | 9/2010 | Blix et al. | |
| 2012/0065633 A1 | 3/2012 | Yagi et al. | |
| 2012/0109116 A1 | 5/2012 | Asconeguy et al. | |
| 2012/0302996 A1 * | 11/2012 | Barash | A61M 25/1018 604/509 |
| 2013/0085493 A1 * | 4/2013 | Bloom | A61B 18/1492 606/41 |
| 2013/0197499 A1 | 8/2013 | Lalonde et al. | |

FOREIGN PATENT DOCUMENTS

| | | |
|---|---|---|
| CA | 2862125 A1 | 8/2013 |
| EP | 0203094 A1 | 12/1986 |

OTHER PUBLICATIONS

International Search Report and Written Opinion dated Jun. 11, 2015, for corresponding International Application No. PCT/CA2015/000166; International Filing Date: Mar. 18, 2015 consisting of 8 pages.
Supplementary Partial European Search Report dated Sep. 19, 2017, for corresponding Application No. EP 15 76 4253.
Supplementary European Search Report, dated Oct. 12, 2017, for corresponding European Application No. EP 15 76 4746, consisting of 7 pages.

* cited by examiner

BALLOON DESIGN TO REDUCE DISTAL LENGTH

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates generally to catheters and methods for performing targeted tissue ablation in a subject. In particular, the present invention provides devices comprising catheters having balloons configured to reduce the distal length of the device and to reduce likelihood of delamination of the balloon from the catheter body.

BACKGROUND OF THE INVENTION

Tissue ablation is used in numerous medical procedures to treat a patient. Ablation can be performed to remove undesired tissue such as cancer cells. Ablation procedures may also involve the modification of the tissue without removal, such as to stop electrical propagation through the tissue in patients with an arrhythmia. The ablation is often performed by passing energy, such as electrical energy, through one or more electrodes causing the tissue in contact with the electrodes to heats up to an ablative temperature, but may also be performed by freezing the tissue with the use of a cryoablation catheter.

Cryoablation catheters typically include an expandable element, such as a balloon, at the distal end. Although there are significant advantages of using balloons for cryoablation techniques, there are often associated disadvantages. First, to provide adequate attachment strength between a balloon and the catheter, the distal end of the balloon is often attached to a device distal tip, which may extend distally beyond the balloon. A balloon catheter with a distal tip can be difficult to position within the body, for example the right or left atrium of the heart. For a cryoablation technique to be effective, the distal end must be articulated with great accuracy to contact the balloon with the target tissue. Additionally, this technique is often performed in a very small space. A catheter with a long distal tip (one that extends past the distal neck of the balloon) or a balloon with extended distal and/or proximal necks can exaggerate steering problems.

Second, there is the concern that the balloon will burst from the application of pressurized cryofluid within, or the seal between the balloon and the body or shaft of the catheter will come undone (delamination). For the typically shaped catheter balloon, a balloon with a conical or ellipsoidal body and two necks, the outward pressure exerted on the balloon pushes the balloon material away from the catheter body or shaft. Longer necks with more attachment surface area are needed to securely attach the balloon to the catheter and prevent delamination due to the forces of pressure. This, in turn, creates longer balloons at the catheter distal tip that are more difficult to steer and precisely contact with target tissue.

In light of the above, it is the object of the present invention to provide a cryoablation catheter with a shortened distal tip that not only is more easily manipulated within small spaces, but that also includes a balloon that is more resistant to delamination from the catheter body or shaft by making use of the balloon pressure to help reduce the tensile stress on the sealing or bonding agent. Currently used devices with balloons having everted necks experience the opposite effect, with the balloon pressure contributing to delamination. Additionally, glue joints are not particularly good at resisting tensile stress, unless in compression. It is another object to provide a method of using a cryoablation catheter with a shortened distal tip.

SUMMARY OF THE INVENTION

The present invention advantageously provides a medical system, specifically a balloon catheter, that is more easily navigated within the body and that includes a balloon that is more resistant to bursting and delamination. In one embodiment, a medical device for thermally affecting tissue may include an elongate body, a shaft that is slidably disposed within the elongate body, an inflatable element (for example, a balloon) defining a chamber and having a proximal neck coupled to the elongate body and forming a proximal seal, and also having a distal neck coupled to the shaft and forming a distal seal that is substantially coterminous with the shaft, the distal seal being between the inflatable element and the shaft and extending within the chamber of the inflatable element. The proximal neck and the distal neck each may include an outer surface and an inner surface, the distal seal being formed between the outer surface of the distal neck and a distal portion of the shaft. The proximal seal may extend within the chamber of the inflatable element. For example, the proximal seal may be formed between the outer surface of the proximal neck and a distal portion of the elongate body. Alternatively, the proximal seal may be external to the chamber of the expandable element and extend along the elongate body in a proximal direction from the chamber of the expandable element. In either embodiment, the proximal seal and the distal seal may each define a length of approximately 10% to 30% of the total length of the expandable element when the expandable element is inflated. The shaft and the expandable element may be coterminous and may define a distal face that is substantially continuous.

In another embodiment, a medical device for thermally affecting tissue may include an elongate body, a shaft that is movably disposed within the elongate body, a first balloon disposed within a second balloon, each balloon defining a chamber and having at least one proximal adhesive junction and at least one distal adhesive junction, the second balloon when expanded defining a substantially continuous surface with the distal end of the shaft. The at least one distal adhesive junction of the first balloon may be between the first balloon and the shaft and extend within the chamber of the first balloon, and the at least one distal adhesive junction of the second balloon may be between the second balloon and the first balloon and extend within the chamber of the first balloon. The first balloon may be asymmetrically positioned within the second balloon, with the at least one proximal adhesive junction of the first balloon being one proximal adhesive junction between the first balloon and the elongate body and extending within the chamber of the first balloon, and the at least one proximal adhesive junction of the second balloon being one proximal adhesive junction between the second balloon and the elongate body and extending proximally along the elongate body external to the chamber of the first balloon. The proximal adhesive junction of the first balloon may be located a distance along the elongate body from the proximal adhesive junction of the second balloon, the distance defining an interstitial space between the first balloon and the second balloon. Further, the at least one distal adhesive junction of the first balloon may define a length that is greater than the length defined by the at least one distal adhesive junction of the second balloon. Alternatively, the first balloon may be symmetrically positioned within the second balloon, with the at least one proximal adhesive junction of the first balloon including an adhesive junction between the first balloon and the elongate body and the second balloon, the at least one proximal adhesive junction of the first balloon and the at least one adhesive junction of the second balloon both extending within the chamber of the first balloon. Alternatively, the first balloon may be symmetrically positioned within the second balloon, the at least one proximal adhesive junction of the first balloon being one proximal adhesive junction between the first balloon and the elongate body and extending within the chamber of the first balloon, and the at least one proximal adhesive junction of the second balloon being one proximal adhesive junction between the second balloon and the elongate body and extending proximally along the elongate body external to the chamber of the first balloon. The at least one distal adhesive junction and the at least one proximal adhesive junction of the first balloon may extend within the chamber of the first balloon each define a length of approximately 10% to 30% of the total inflated balloon length. Further, the second balloon may define a distal face when inflated, and the shaft may be coterminous with the distal face.

In another embodiment, a medical device for thermally affecting tissue may include: an elongate body defining a proximal portion, a distal portion, and a lumen therebetween; a shaft slidably disposed within the catheter body lumen, the shaft defining a proximal portion and a distal portion; a first balloon disposed within a second balloon, each balloon defining a chamber and having a proximal neck coupled to the distal portion of catheter body to form a proximal seal, and each balloon having a distal neck coupled to the distal portion of the shaft to form a distal seal that is substantially coterminous with the distal portion of the shaft; a fluid injection conduit disposed within the chamber of the first balloon; the first balloon being symmetrically positioned within the second balloon, with the proximal seal of the first balloon comprising an adhesive junction between the first balloon and the distal portion of the catheter body and extending within the chamber of the first balloon, and the proximal seal of the second balloon comprising an adhesive junction between the second balloon and the distal portion of the catheter body at a distance proximal to the proximal seal of the first balloon, the proximal seal of the second balloon extending externally to the chamber of the first balloon; the at least one distal seal of the first balloon comprising an adhesive junction between the first balloon and the distal portion of the shaft and also comprising an adhesive junction between the first and second balloons, the distal seal of the first balloon extending within the chamber of the first balloon; the second balloon defining a distal face when inflated, the shaft being coterminous with the distal face; and the proximal seal and the distal seal of the first balloon each defining a length of approximately 10% to 30% of the inflated balloon length.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1A:
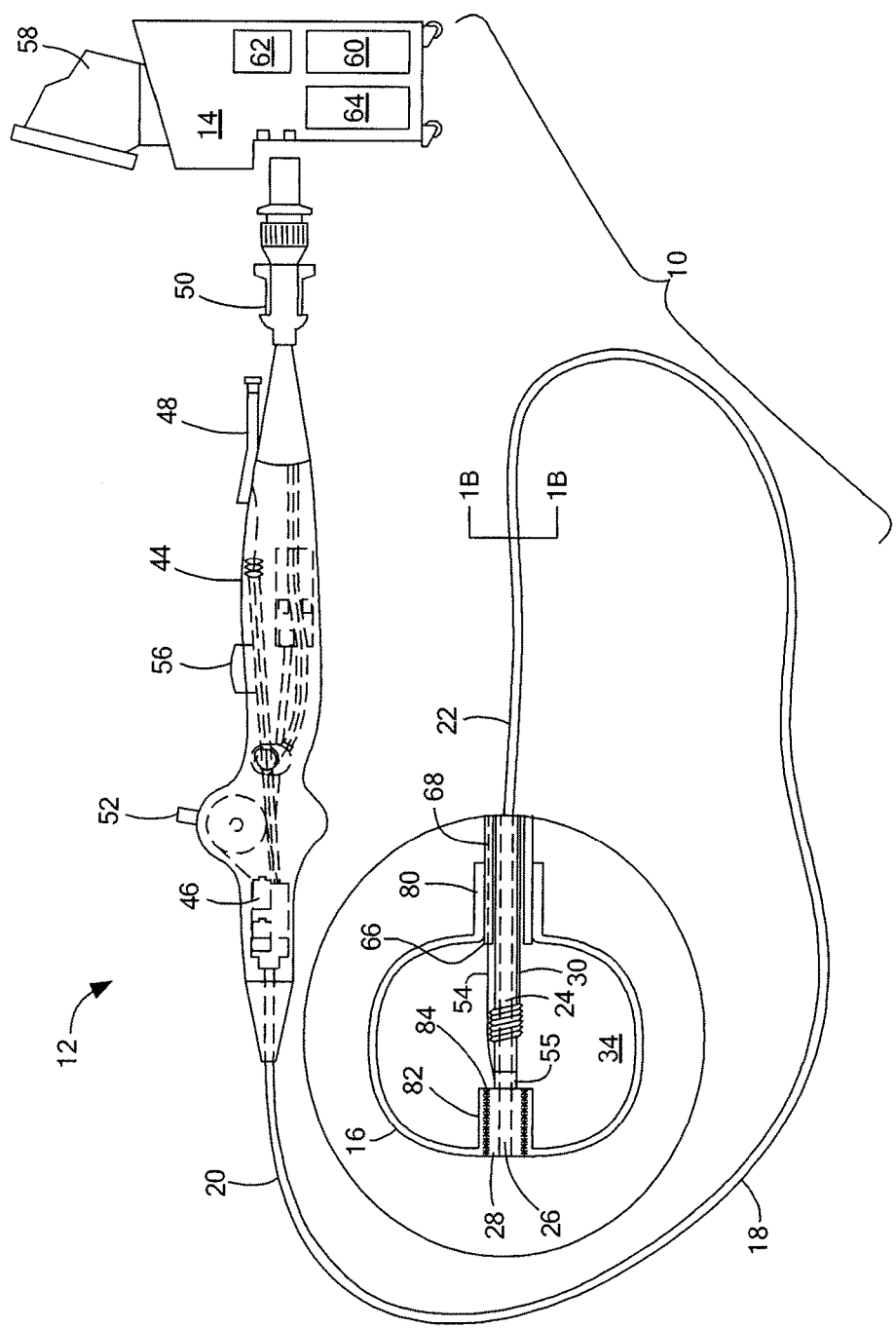
FIG. 1A is an illustration of a generalized medical system constructed in accordance with the principles of the present invention.

The present invention advantageously provides a medical system, specifically, a balloon catheter, that is more easily navigated within the body of a patient and that includes a balloon that is more resistant to bursting and delamination. Referring now to the drawing figures in which like reference designations refer to like elements, an embodiment of a medical system constructed in accordance with principles of the present invention is shown in FIG. 1A and generally designated as "10." The system 10 generally includes a medical device 12 that may be coupled to a control unit 14 or operating console. The medical device 12 may generally include one or more treatment regions, including at least one balloon 16, for energetic or other therapeutic interaction between the medical device 12 and a treatment site. The treatment region(s) may deliver, for example, cryogenic therapy, radio frequency energy, or other energetic transfer with a tissue area in proximity to the treatment region(s), including cardiac tissue.

The medical device 12 may include an elongate body 18 passable through a patient's vasculature and/or proximate to a tissue region for diagnosis or treatment, such as a catheter, sheath, or intravascular introducer. The elongate body 18 may define a proximal portion 20 and a distal portion 22, and may further include one or more lumens disposed within the elongate body 18 thereby providing mechanical, electrical, and/or fluid communication between the proximal portion of the elongate body 18 and the distal portion of the elongate body 18, as discussed in more detail below.

The medical device 12 may include a rigid or semi-rigid shaft 24 at least partially disposed within a portion of the elongate body 18. The shaft 24 may extend or otherwise protrude from a distal end of the elongate body 18, and may be movable with respect to the elongate body 18 in longitudinal and rotational directions. That is, the shaft 24 may be slidably and/or rotatably moveable with respect to the elongate body 18. The shaft 24 may further define a lumen 26 therein for the introduction and passage of a guide wire. The shaft 24 may comprise a plurality of sections, each section having a varying diameter, with the shaft terminating in or otherwise including an area having a larger diameter than the rest of the shaft 24, which may be referred to as a distal tip 28. The distal tip 28 may define an opening and passage therethrough that is in communication with the shaft lumen 26. As discussed in greater detail below, the balloon 16 may be attached to the distal tip 28. However, it will be understood that the shaft 24 may have a single continuous diameter with the balloon 16 being attached to the shaft proximate the distal end of the shaft.

Figure 4:
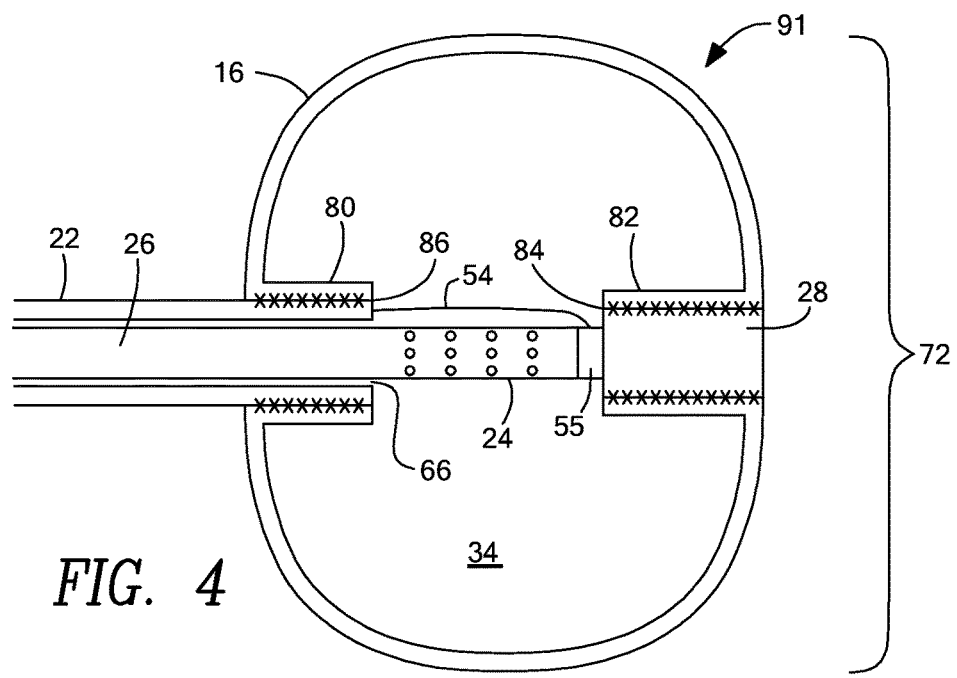
FIG. 4 is a cross-sectional view of the first embodiment of the medical device of FIG. 2, in which the both the proximal and distal necks are inverted.

The medical device 12 may further include a fluid delivery conduit 30 traversing at least a portion of the elongate body 18 and towards the distal portion 22. The delivery conduit 30 may be coupled to or otherwise extend from the distal portion 22 of the elongate body 18 into the balloon 16. The delivery conduit 30 may, for example, be wrapped or coiled about at least a portion of the shaft 24 within the balloon, as shown in FIG. 1A. Alternatively, the delivery conduit 30 may be otherwise coupled to the shaft 24 of the medical device 12, or may be disposed within the shaft 24 with the shaft defining one or more openings through which fluid may pass into the balloon (for example, as shown in FIG. 4). Alternatively, the fluid delivery conduit 30 may be flexible, constructed from a shape memory material (such as Nitinol), and/or include other controllably deformable materials that allow the fluid delivery conduit 30 to be manipulated into a plurality of different geometric configurations, shapes, and/or dimensions. Although a fluid delivery conduit is not expressly shown in FIGS. 5-9 for simplicity, it will be understood that the devices shown in all figures may have any suitable, fluid delivery conduit including those shown in FIGS. 1A and 4.

The fluid delivery conduit 30 may define a lumen therein for the passage or delivery of a fluid from the proximal portion of the elongate body 18 and/or the control unit 14 to the distal portion and/or treatment region of the medical device 12. The fluid delivery conduit 30 may further include one or more apertures or openings therein to provide for the dispersion or directed ejection of fluid from the lumen to the interior chamber 34 of the balloon 16. 24

The medical device 12 may further include a handle 44 coupled to the proximal portion 20 of the elongate body 18. The handle 44 can include circuitry for identification and/or use in controlling of the medical device 12 or another component of the system 10. For example, the handle 44 may include one or more pressure sensors 46 to monitor the fluid pressure within the medical device 12. Additionally, the handle 44 may be provided with a fitting 48 for receiving a guide wire that may be passed into the guide wire lumen 26.

The handle 44 may also include connectors 50 that are matable directly to a fluid supply/exhaust and control unit 14 or indirectly by way of one or more umbilicals. The handle 44 may further include blood detection circuitry in fluid and/or optical communication with the injection, exhaust and/or interstitial lumens. The handle 44 may also include a pressure relief valve in fluid communication with the fluid delivery conduit 30 and/or exhaust lumen to automatically open under a predetermined threshold value in the event that value is exceeded.

The handle 44 may also include one or more actuation or control features that allow a user to control, deflect, steer, or otherwise manipulate a distal portion of the medical device from the proximal portion of the medical device. For example, the handle 44 may include one or more components such as a lever or knob 52 for manipulating the elongate body 18 and/or additional components of the medical device 12. For example, a pull wire with a proximal end and a distal end may have its distal end anchored to the elongate body 18 at or near the distal portion 22. A proximal end of the pull wire 54 may be anchored to an element such as a cam in communication with and responsive to the lever 52. A distal end of the pull wire 54 may be attached or coupled to a portion of elongate body 18 or the shaft 24. As a non-limiting example, the pull wire 54 may be coupled to a coupling element 55 that is, in turn, coupled to the shaft 24 (as shown in the figures). However, it will be understood that the pull wire 54 may be coupled to the device in any manner suitable to create at least one point of inflection (that is, a location at which the device may bend during navigation through the patient's vasculature) in a desired location on the elongate body 18 and/or the treatment element. The medical device 12 may include an actuator element 56 that is movably coupled to the proximal portion of the elongate body 18 and/or the handle 44. The actuator element 56 may further be coupled to a proximal portion of the shaft 24 such that manipulating the actuator element 56 in a longitudinal direction causes the shaft 24 to slide towards either of the proximal or distal portions of the elongate body 18. The actuator element 56 may include a thumb-slide, a push-button, a rotating lever, or other mechanical structure for providing a movable coupling to the elongate body 18, the handle 44, and/or the shaft 24. Moreover, the actuator element 56 may be movably coupled to the handle 44 such that the actuator element is movable into individual, distinct positions, and is able to be releasably secured in any one of the distinct positions. The handle 44 may also include one or more rotational actuator elements for rotating the shaft 24 and/or a guide wire.

The control unit 14 may include one or more computers 58 that include one or more processors for receiving signals from one or more sensors throughout the system 10, and or for the automatic, semi-automatic, and/or manual operation of the system. For example, the system 10 may include one or more computers 58 having one or more user input devices by which a user can program system parameters such as the inflation and deflation of a balloon, circulation of coolant through the fluid delivery and recovery conduits, and/or the operation of one or more electrodes or other thermal delivery elements. Additionally, the user may use the user input devices to override the automatic operation of the system 10 either programmed into or predetermined by the control unit 14.

The system 10 may further include one or more sensors to monitor the operating parameters throughout the system, including for example, pressure, temperature, flow rates, volume, or the like in the control unit 14 and/or the medical device 12, in addition to monitoring, recording or otherwise conveying measurements or conditions within the medical device 12 or the ambient environment at the distal portion of the medical device 12. The sensor(s) may be in communication with the control unit 14 for initiating or triggering one or more alerts or therapeutic delivery modifications during operation of the medical device 12. One or more valves, controllers, or the like may be in communication with the sensor(s) to provide for the controlled dispersion or circulation of fluid through the lumens/fluid paths of the medical device 12. Such valves, controllers, or the like may be located in a portion of the medical device 12 and/or in the control unit 14.

In an exemplary system, a fluid supply 60 including a coolant, cryogenic refrigerant, or the like, an exhaust or scavenging system for recovering or venting expended fluid for re-use or disposal, as well as various control mechanisms for the medical system may be housed in the control unit 14. In addition to providing an exhaust function for the catheter fluid supply, the console may also include pumps, valves, controllers or the like to recover and/or re-circulate fluid delivered to the handle, the elongate body, and/or the fluid pathways of the medical device 12. A vacuum pump 62 in the control unit 14 may create a low-pressure environment in one or more conduits within the medical device 12 so that fluid is drawn into the conduit(s)/lumen(s) of the elongate body 18, away from the distal portion and towards the proximal portion of the elongate body 18. For example, the control unit 14 may include a fluid recovery reservoir 64 that is in fluid communication with a fluid recovery conduit 66 that is, in turn, in fluid communication with the balloon 16. The control unit 14 may include one or more controllers, processors, and/or software modules containing instructions or algorithms to provide for the automated operation and performance of the features, sequences, or procedures described herein.

While the medical device 12 may be in fluid communication with a cryogenic fluid source to cryogenically treat selected tissue, it is also contemplated that the medical device 12 may alternatively or additionally include one or more electrically conductive portions or electrodes thereon coupled to a radio frequency generator or power source as a treatment or diagnostic mechanism.

Figure 1B:
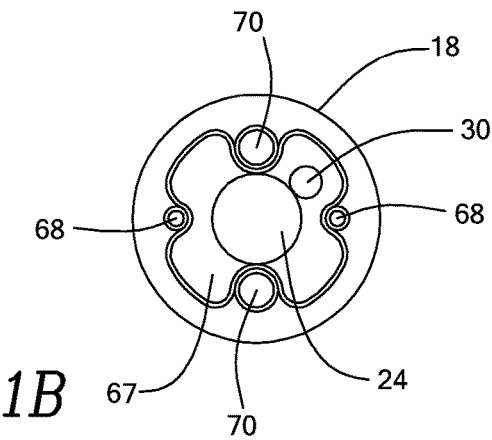
FIG. 1B is a cross-sectional view of the elongate body of a medical device.

Referring now to FIG. 1B, a non-limiting cross-sectional view of the elongate body 18 of the device is shown. The elongate body 18 may generally include an inner lumen 67, one or more pull wire lumens 68, and, optionally, one or more outer lumens 70. The inner lumen 67 may be sheathed by or defined by a layer of braided wire and/or a layer of Teflon (not shown for simplicity). The sheath 24 and fluid delivery conduit 30 may be disposed within the inner lumen 67, and the space within the inner lumen 67 surrounding the sheath 24 may be in communication with the vacuum 62 for the removal of expanded coolant from the distal end of the device. One or more pull wires 54 may be located within the one or more pull wire lumens 68 on the outside of the inner lumen 67, although the pull wire 54 is shown in FIGS. 1A and 4-9 The one or more outer lumens 70 may serve as conduits for additional fluids, wires, sensors, or the like. However, it will be understood that other suitable configurations of interior components and lumens may also be used.

Referring now to FIGS. 1A through 9, at least one balloon 16 may be at the distal portion of the medical device 12. The at least one balloon 16 may be coupled to a portion of the elongate body 18 and also coupled to a portion of the shaft 24 to contain a portion of the fluid delivery conduit 30 therein, as shown and discussed in more detail in FIGS. 2-9.

Each balloon 16 may each define an interior chamber or region 34. For example, coolant or fluid dispersed from the fluid delivery conduit 30 may circulate within the interior chamber 34, and the interior chamber 34 may be in fluid communication with the fluid recovery conduit 66 defined by or included in the elongate body 18 for the removal of dispersed coolant from the interior chamber 34 of the balloon 16. In embodiments in which the device 12 includes more than one balloon, an additional fluid delivery conduit and/or fluid recovery conduit may fluidly connect the additional balloons to the control unit 14. The at least one balloon 16 may further include one or more material layers providing for puncture resistance, radiopacity, or the like.

Figure 2:
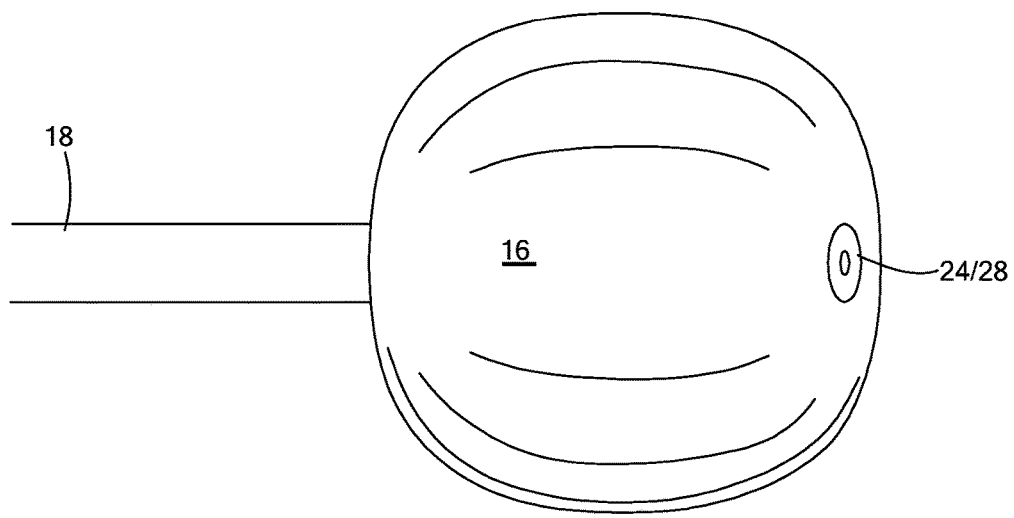
FIG. 2 is a perspective view of a first embodiment of a medical device, in which both the proximal and distal necks are inverted.
Figure 3:
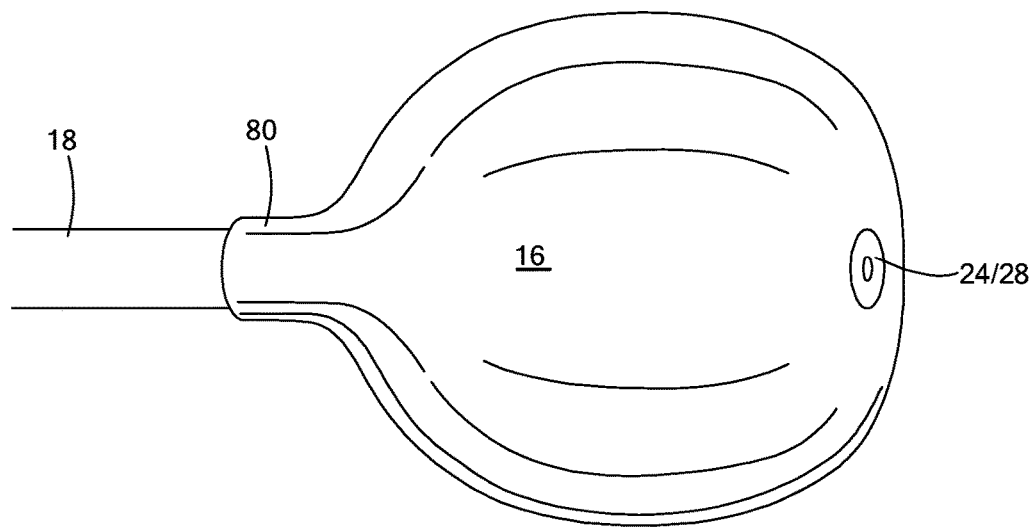
FIG. 3 is a perspective view of a second embodiment of a medical device, in which the proximal neck is everted and the distal neck is inverted.

As shown in FIGS. 2-9, the distal end of the shaft 24, for example, the distal tip 28, may be rounded to match the curvature of a balloon 16 when inflated, such that the balloon 16 may define a distal face 72 having a substantially continuous surface, without the shaft 24 protruding beyond the balloon distal face 72. Further, the distal tip 28 or distal end of the shaft 24 may be manufactured with a curved distal surface that matches a curve in the balloon distal face 72, enhancing the continuity between the shaft 24 and the distal face 72. The shaft is depicted in FIGS. 2 and 3 as "24/28" to include embodiments in which the balloon 16 is generally coupled to the distal portion of the shaft 24 and embodiments in which the balloon 16 is coupled to a distal tip 28 in particular. As a non-limiting embodiment, the distal face 72 may be slightly curved or arcuate, creating an atraumatic surface for safe navigation through the patient's vasculature and within the patient's heart. A substantially continuous arcuate surface without any projections may facilitate steering of the distal end of the medical device within the patient, especially in small spaces such as the chambers of the heart or vasculature. Although the balloon is shown in the figures as having a substantially spherical or rounded cubic shape, it will be understood that the balloon may have any suitable shape that allows for the inclusion of a shortened distal tip.

Figure 5:
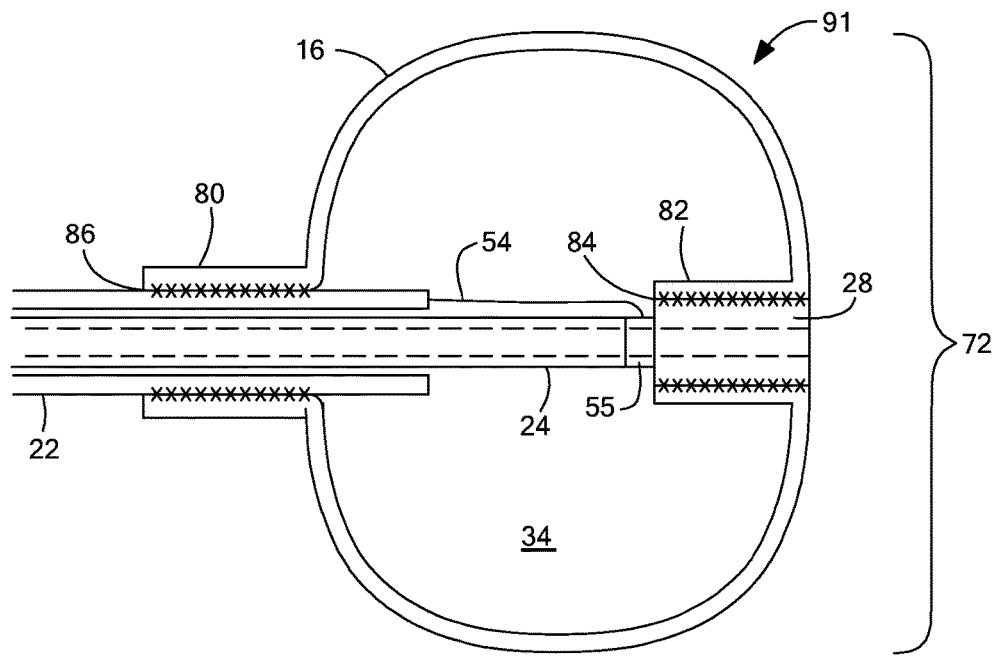
FIG. 5 is a cross-sectional view of the second embodiment of the medical device of FIG. 3, in which the proximal neck is everted and the distal neck is inverted.

The medical device 12 may include a single balloon 16, as seen in FIGS. 4 and 5. The balloon 16 may have a proximal neck 80 at which the balloon 16 is coupled, by an adhesive junction or other joining means, to the distal portion 22 of the elongate body 18, and may further have a distal neck 82 at which the balloon 16 is coupled, by an adhesive junction or other joining means, to a distal portion of the shaft 24, such as the distal tip 28. The distal neck 82 of the balloon 16 may be turned inward (in a distal-to-proximal direction) extending within the chamber 34 of the balloon 16. This may be referred to as the distal neck 82 being inverted. The inward extension of the distal neck 82 may form a distal seal 84 that is substantially coterminous with the shaft 24, and may define a length of approximately 10% to 30% of the total length of the balloon 16 when the balloon is in an inflated state. The length of the inflated and uninflated balloon may be measured as a straightline distance between the proximalmost point and the distalmost point of the balloon 16. In the figures, all seals, which may also be referred to as "adhesive junctions," are stylistically depicted with hash marks for clarity.

As seen in FIG. 4, the expandable element may be substantially toroidal in shape, with the proximal neck 80 also being inverted (that is, turned inward, extending in a proximal-to-distal direction). In this configuration, an outer surface of the proximal neck 80 may be bonded, adhered, or otherwise in contact with and attached to an outer surface of the distal portion 22 of the elongate body 18 to create a proximal seal 86 extending within the balloon interior chamber 34. The proximal seal 86 may define a length of approximately 10% to 30% of the total length of the balloon 16 when in an inflated state. Alternatively, as seen in FIG. 5, the balloon 16 may include a proximal neck 80 that is everted (that is, turned outward, extending in a distal-to-proximal direction). In this configuration, an inner surface of the proximal neck 80 may be bonded, adhered, or otherwise in contact with and attached to an outer surface of the distal portion 22 of the elongate body 18 to create a proximal seal 86 extending without (that is, being external to) the balloon interior chamber 34 along an outer surface of the distal portion 22 of the elongate body 18. Further, the proximal neck 80 may be coupled to the distal portion 22 of the elongate body 18 such that the proximal neck 80 (proximate the balloon chamber 34) and the elongate body 18 are coterminous (for example, as shown in FIG. 4), or the proximal neck 80 may be coupled to the distal portion 22 of the elongate body 18 such that a portion of the elongate body 18 extends within the chamber 34 (for example, as shown in FIG. 5). In all embodiments, the balloon 16 may define a distal face 72 that has a substantially continuous surface that facilitates navigation of the device within the patient.

The medical device 12 may include more than one balloon. For example, FIGS. 6-9 show a medical device 12 having an inner balloon 88 and an outer balloon 90. The inner 88 and outer 90 balloons together may comprise the treatment element 91. The inner balloon 88 may contain a portion of the fluid delivery conduit 30 therein, and the outer balloon 90 may be disposed about the inner balloon 88. The inner 88 and outer 90 balloons in FIGS. 6-9 may be substantially similar to the single balloon 16 shown and described in the other figures, in composition, function, attachment, etc. The inner 88 and outer 90 balloons may be located substantially adjacent to or in contact with each other, and may define an interstitial space 92 between the balloons 88, 90 to facilitate detection and prevention of leaks from the first 88. For example, one or more sensors (such as impedance sensors, pressure sensors, and/or temperature sensors) may be located within the interstitial space to detect fluid leaks. In the embodiments shown in FIGS. 6 and 8, the interstitial space 92 may be very thin, even absent in some areas, especially when the inner balloon 88 is inflated and in contact with the outer balloon 90. In the embodiments shown in FIGS. 7 and 9, however, the interstitial space 92 may be larger in at least a portion of the treatment element. The two-balloon configuration may add strength to the treatment element, in that a delamination force resulting from inflation of the inner balloon 88 would have to overcome the seals of both the inner and outer balloons for the treatment element 91 to delaminate.

As shown in FIGS. 6-9, each of the inner 88 and outer 90 balloons may have a proximal neck 94, 96 coupled to an outer surface of the distal portion 22 of the elongate body 18, and a distal neck 98, 100 coupled to a portion of the shaft 24, for example, the distal tip 28. In all of FIGS. 6-9, the outer balloon 90 may define a distal face 72 that has a substantially continuous surface that facilitates navigation of the device within the patient. For example, the shaft 24 or distal tip 28 may be substantially coterminous with the distal balloon 90.

Continuing to refer to FIGS. 6-9, the inner balloon 88 may be substantially toroidal in shape, with the proximal neck 94 being inverted (that is, turned inward, in a proximal-to-distal direction) to form a first proximal seal 102 between an outer surface of the proximal neck 94 and an outer surface of the distal portion 22 of the elongate body 18, and the distal neck 98 being inverted (that is, turned inward, in a distal-to-proximal direction) to form a first distal seal 104 between an outer surface of the distal neck 98 and a distal portion of the shaft 24 (for example, the distal tip 28), each seal 102, 104 extending within the interior chamber 34 of the inner balloon 88. Although the seals 102, 104 could also be described as extended within the interior chamber of the second balloon 90, the description is limited to extension within the interior chamber 34 of the inner balloon 88 for simplicity of reference. As is discussed in more detail below, the first proximal seal 102 and the first distal seal 104 of the inner balloon 88 may be attached to the elongate body 18 and shaft 24, respectively. A second portion of each neck 94, 98 may be in contact with or substantially in contact with, but not attached to, a portion of the proximal and distal necks of the outer balloon 90. As such, fluid leaking from the inner balloon 88 may more easily flow between the inner 88 and outer 90 balloons for detection by a leak-detection sensor disposed in the interstitial space 92, such as a pressure or impedance sensor. The distal neck 98 and proximal neck 94 of the inner balloon 88 may each define a length of approximately 10% to 30% of the total length of the inner balloon 88 when the inner balloon 88 is in an inflated state, with the length of each neck 94, 98 being measured as a straightline distance between the proximalmost point and the distalmost point of the inner balloon 88.

The distal neck 100 of the outer balloon 90 may also be inverted (that is, turned inward, in a distal-to-proximal direction), extending within the interior chamber 34 of the inner balloon 88. An outer surface of the distal neck 100 of the outer balloon 90 may be bonded, adhered, or otherwise in contact with and attached to an outer surface of a distal portion of the shaft 24 (for example, the distal tip 28) to create a distal seal 110 extending within the interior chamber 34 of the inner balloon 88. An inner surface of distal neck 100 of the outer balloon 90 may also be in contact with or substantially in contact with, but not attached to, an outer surface of the distal neck 98 of the inner balloon 88. At least a portion of the distal neck 98 of the inner balloon 88 may overlap the inverted distal neck 100 of the outer balloon 90.

Figure 6:
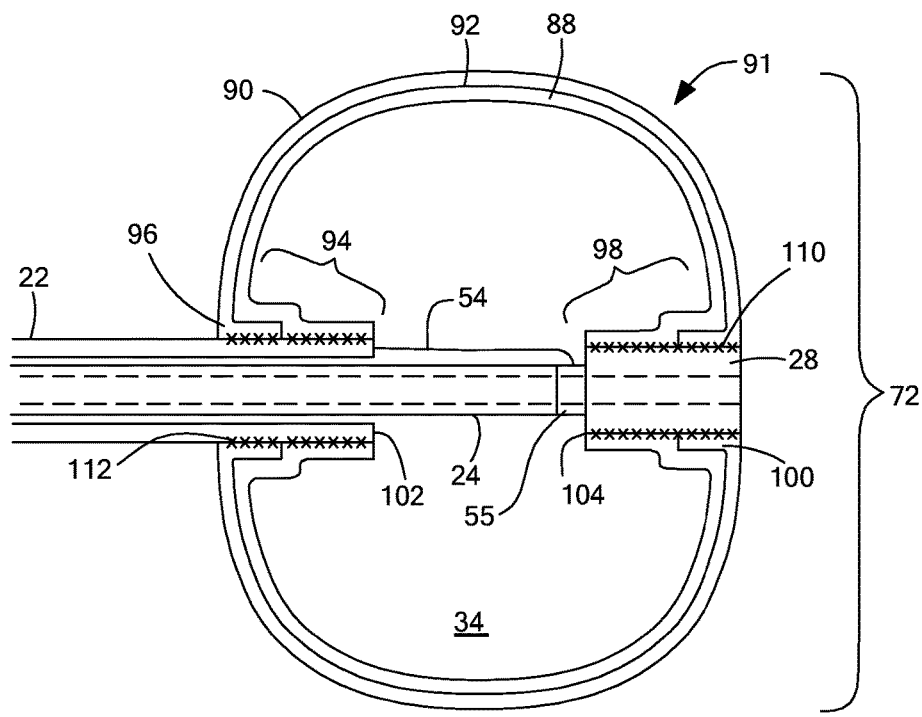
FIG. 6 is a cross-sectional view of a third embodiment of a medical device, the device having two balloons with a first balloon symmetrically positioned within a second balloon and the proximal and distal necks of both balloons being inverted.
Figure 7:
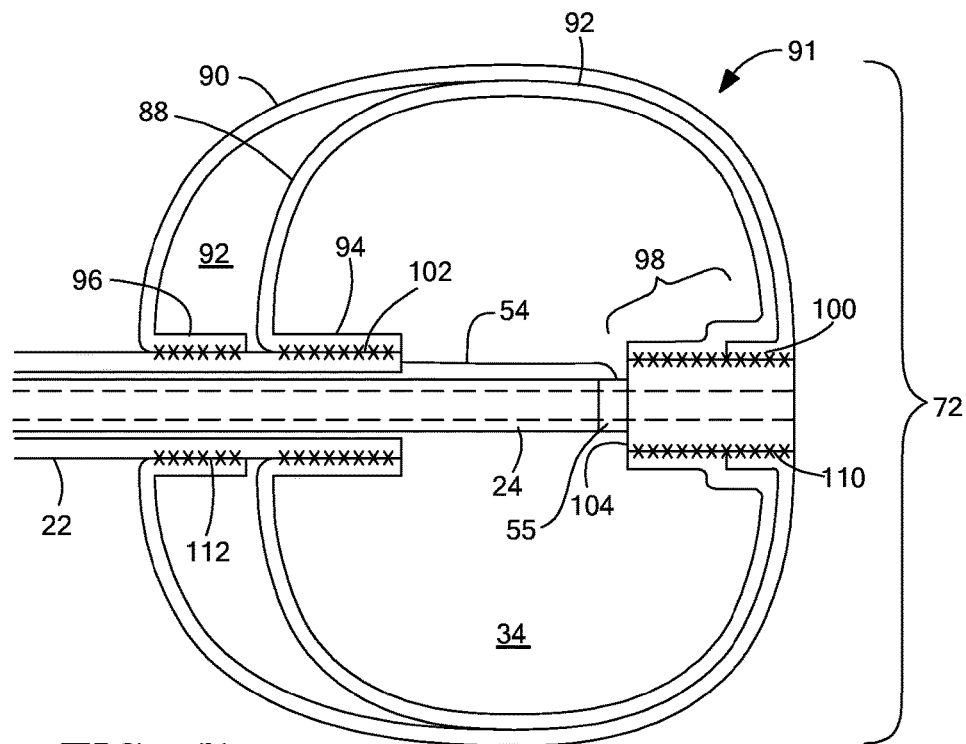
FIG. 7 is a cross-sectional view of a fourth embodiment of a medical device, the device having two balloons with a first balloon asymmetrically positioned within a second balloon and the proximal and distal necks of both balloons being inverted.

Now referring in particular to FIGS. 6 and 7, the proximal neck 96 of the outer balloon 90 may also be inverted (that is, turned inward, in a proximal-to-distal direction), extending within the interior chamber 34 of the inner balloon 88. An outer surface of the outer balloon proximal neck 96 may be bonded, adhered, or otherwise in contact with and attached to an outer surface to the distal portion 22 of the elongate body 18 to form a proximal seal 112. The inner balloon 88 may be symmetrically or asymmetrically positioned within the outer balloon 90, depending on, for example, the desired maneuverability of the device, the procedure for which the device is used, and/or the desired cooling effect of the treatment element. For example, the device shown in FIG. 6 may have a more distal deflection point than the device shown in FIG. 7, because the layered proximal necks 94, 96 of the inner 88 and outer 90 balloons may increase the stiffness and decrease the flexibility of the device at or near the location at which the proximal necks 94, 96 are attached to the elongate body 18. This more distal deflection point may allow the device to be navigated through tortuous vasculature more easily. Additionally, the asymmetrical configuration shown in FIG. 7 may affect the cooling capacity of the treatment element 91. The larger interstitial space 92 between the inner 88 and outer 90 balloons may provide thermal insulation of the inner balloon 88, particularly the proximal portion of the inner balloon 88, from the warming effect of the surrounding blood. This, in turn, may enhance the cooling effect of, at least, the distal portion of the treatment element through the outer balloon 90. That is, the limited heat transfer from tissue to the proximal portion of the inner balloon 88 may preserve and potentially concentrated the cooling capacity within the distal portion of the treatment element 91. The symmetrical configuration shown in FIG. 6 may allow cooling of both the proximal and distal portions of the treatment element 91. In a non-limiting embodiment, this symmetrical configuration may be useful when the device is inserted into the left atrium through a pulmonary vein, and then retracted so that the proximal portion of the treatment element 91 is in contact with the pulmonary vein ostium. In that case, the proximal portion, rather than the distal portion, of the treatment element 91 may be used to thermally treat the pulmonary vein ostium.

FIG. 6 shows a configuration in which the inner balloon 88 is symmetrically positioned within, and concentric with, the outer balloon 90. Both the inner 88 and outer 90 balloons in FIG. 6 may be toroidal in shape, with the proximal necks 94, 96 and distal necks 98, 100 of the balloons being inverted and extending within the interior chamber 34 of the inner balloon 88. In such an embodiment, an inner surface of the proximal neck 96 of the outer balloon 90 may be in contact with or substantially in contact with, but not attached to, an outer surface of the proximal neck 94 of the inner balloon 88. At least a portion of the proximal neck 94 of the inner balloon 88 may overlap the proximal neck 96 of the outer balloon 90. In this manner, a double-layered adhesive junction may be formed, which may further prevent delamination or tearing from occurring when the balloons are inflated and burst pressure is exerted.

FIG. 7 shows a configuration in which the inner balloon 88 may be asymmetrically positioned within the outer balloon 90. Both the inner 88 and outer 90 balloons may be toroidal in shape, but may not be concentric, unlike the configuration shown in FIG. 6. In the configuration shown in FIG. 7, the proximal neck 96 of the outer balloon 90 may be bonded, adhered, or otherwise in contact with and attached only to the distal portion 22 of the elongate body 18, without being overlapped by and coupled to at least a portion of the proximal neck 94 of the inner balloon 88. Further, the proximal neck 96 of the outer balloon 90 may not extend within the interior chamber 34 of the inner balloon 88, but may instead extend within the interstitial space 92 between the inner 88 and outer 90 balloons. Defined another way, the proximal neck 96 of the outer balloon 90 may be inverted within the treatment element 91 as a whole. As shown in FIG. 7, the portion of interstitial space 92 proximate the proximal necks 94, 96 of the inner 88 and outer 90 balloons may be larger than the portion of interstitial space 92 proximate the distal necks 98, 100 of the inner 88 and outer 90 balloons. This size of the interstitial space 92 proximal the proximal necks 94, 96 may be determined by the distance between the proximal seal 102 of the inner balloon 88 and the proximal seal 112 of the outer balloon 90.

Figure 8:
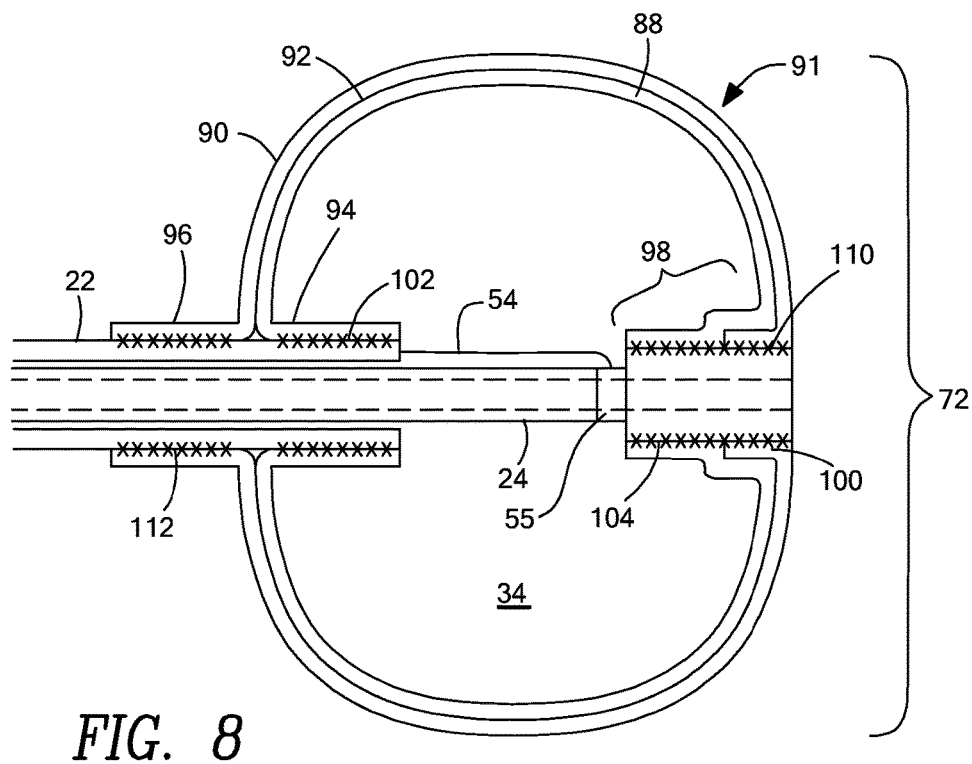
FIG. 8 is an illustration of a cross-sectional view of a fifth embodiment of a medical device, the device having two balloons with a first balloon symmetrically positioned within a second balloon and the distal necks of both balloons being inverted, the proximal neck of the first balloon being inverted, and the proximal neck of the second balloon being everted.
Figure 9:
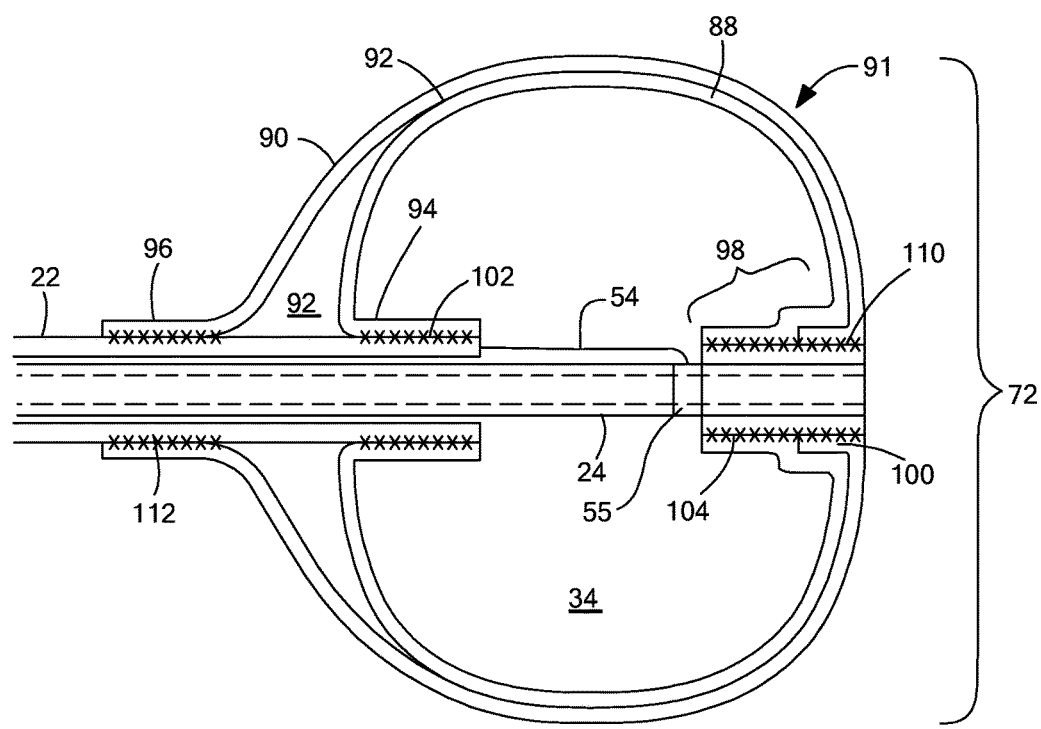
FIG. 9 is a cross-sectional view of a sixth embodiment of a medical device, the device having two balloons with a first balloon asymmetrically positioned within a second balloon and the distal necks of both balloons being inverted, the proximal neck of the first balloon being inverted, and the proximal neck of the second balloon being everted.

Referring now to FIGS. 8 and 9, the proximal neck 96 of the outer balloon 90 may be everted (that is, turned outward, in a distal-to-proximal direction), extending without or being external to both the interior chamber 34 of the inner balloon 88 and the interstitial space 92 between the inner 88 and outer balloons 90. Defined another way, the proximal neck 96 of the outer balloon 90 may be everted on the outside of the treatment element 91 as a whole. An inner surface of the proximal neck 96 of the outer balloon 90 may be bonded, adhered, or otherwise in contact with and attached to the distal portion 22 of the elongate body 18 to form a first proximal seal 112. The inner balloon 88 may be symmetrically or asymmetrically positioned within the outer balloon 90, with the advantages of each configuration being as discussed above regarding FIGS. 6 and 7.

FIG. 8 shows a configuration in which the inner balloon 88 is symmetrically positioned within, and concentric with, the outer balloon 90. In such an embodiment, the proximal neck 96 of the outer balloon 90 may not be coupled to the proximal neck 94 of the inner balloon 88, but the proximal seal 112 of the outer balloon 90 and the proximal seal 102 of the inner balloon 88 may be substantially adjacent to each other, extending in opposite directions. For example, as shown in FIG. 8, the proximal seal 112 of the outer balloon 90 may extend be everted (that is, external to the treatment element 91) in a distal-to-proximal direction, and the proximal seal 102 of the inner balloon 88 may be inverted and extend within the interior chamber 88 (and the treatment element 91 as a whole) in a proximal-to-distal direction. The interstitial space 92 defined between the inner 88 and outer 90 balloons may only be wide enough to facilitate leak detection or leak containment within the outer balloon 90.

FIG. 9 shows a configuration in which the inner balloon 88 is asymmetrically positioned within the outer balloon 90. In such an embodiment, the proximal neck 96 of the outer balloon 90 may be coupled only to an outer surface of the distal portion 22 of the elongate body 18, without being coupled to the proximal neck 94 of the inner balloon 88. As shown in FIG. 9, the portion of interstitial space 92 proximal the proximal necks 94, 96 of the inner 88 and outer 90 balloons may be larger than the portion of interstitial space 92 proximate the distal necks 98, 100 of the inner 88 and outer 90 balloons. The size of the interstitial space 92 between the proximal necks 94, 96 may be determined by the distance between the proximal seal 102 of the inner balloon 88 and the proximal seal 112 of the outer balloon 90.

The continuously arcuate configuration of the distal portion of the medical device generally provides the ability to deliver therapeutic treatment more precisely, because of the absence of a protruding distal tip enhances ease of navigating the device. Further, shape and seal characteristics of the balloons allow for a more even distribution of pressure exerted by the cryogenic fluid. Balloons with outward seals often experience delamination and bursting because all the pressure exerted within the balloon is pushing outward, essentially pulling the balloon away from the medical device. In contrast, the seals of balloons as presented herein are strengthened with increased pressure because the cryogenic fluid, as it is expelled in an outward direction and deflected from the balloon surface within the chamber of the balloon, presses against the inverted necks and reinforces the seals. Although not expressly shown, it will be understood that a configuration may be presented in which the distal necks 98, 100 of the inner 88 and outer 90 balloons may be inverted, whereas both proximal necks 94, 96 may be everted and attached to the device in the manner shown and described in FIGS. 6-9).

It will be appreciated by persons skilled in the art that the present invention is not limited to what has been particularly shown and described herein above. In addition, unless mention was made above to the contrary, it should be noted that all of the accompanying drawings are not to scale. Of note, the system components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein. Moreover, while certain embodiments or figures described herein may illustrate features not expressly indicated on other figures or embodiments, it is understood that the features and components of the system and devices disclosed herein are not necessarily exclusive of each other and may be included in a variety of different combinations or configurations without departing from the scope and spirit of the invention. A variety of modifications and variations are possible in light of the above teachings without departing from the scope and spirit of the invention, which is limited only by the following claims.

What is claimed is:

1. A medical device for thermally affecting tissue comprising:
   an elongate body;
   a shaft disposed in the elongate body and being movable relative to the elongate body when the device is in use, the shaft having a distalmost end face; and
   a first balloon disposed within a second balloon, each balloon defining a chamber and having a proximal adhesive junction and a distal adhesive junction, the second balloon when expanded having a curvature and a distal face, the distalmost end face of the shaft being curved such that distal face of the second balloon when inflated and the distalmost end face of the shaft together define a continuous curved surface, each of the first balloon and the second balloon having an outer surface, the distal adhesive junction of the first balloon being between the outer surface of the first balloon and the shaft, and the distal adhesive junction of the second balloon being between the outer surface of the second balloon and the shaft.

2. The medical device of claim 1, wherein the distal adhesive junction of the first balloon extends within the chamber of the first balloon, and the distal adhesive junction of the second balloon extends within the chamber of the first balloon.

3. The medical device of claim 2, wherein the first balloon is asymmetrically positioned within the second balloon, with the proximal adhesive junction of the first balloon being between the first balloon and the elongate body and extending within the chamber of the first balloon, and proximal adhesive junction of the second balloon being between the second balloon and the elongate body and extending proximally along the elongate body external to the chamber of the first balloon.

4. The medical device of claim 2, wherein the proximal adhesive junction of the first balloon is located a distance along the elongate body from the proximal adhesive junction of the second balloon, the distance defining an interstitial space between the first balloon and the second balloon.

5. The medical device of claim 3, wherein the distal adhesive junction of the first balloon defines a length and the distal adhesive junction of the second balloon defines a length, the length of the distal adhesive junction of the first balloon being greater than the length defined by the distal adhesive junction of the second balloon.

6. The medical device of claim 2, wherein the first balloon is symmetrically positioned within the second balloon, with the proximal adhesive junction of the first balloon being between the first balloon and the elongate body, the proximal adhesive junction of the first balloon and the adhesive junction of the second balloon both extending within the chamber of the first balloon.

7. The medical device of claim 5, wherein the first balloon is symmetrically positioned within the second balloon, the proximal adhesive junction of the first balloon being between the first balloon and the elongate body and extending within the chamber of the first balloon, and the proximal adhesive junction of the second balloon being between the second balloon and the elongate body and extending proximally along the elongate body external to the chamber of the first balloon.

8. The medical device of claim 2, wherein the distal adhesive junction and the proximal adhesive junction of the first balloon extending within the chamber of the first balloon each define a length of approximately 10% to 30% of a total inflated balloon length.

9. The medical device of claim 1, wherein the second balloon defines a distal face when inflated, the shaft being coterminous with the distal face.

10. A medical device for thermally affecting tissue comprising:
    an elongate body defining a proximal portion, a distal portion, and a lumen therebetween;
    a shaft slidably disposed within the catheter body lumen, the shaft defining a proximal portion and a distal portion;
    a first balloon disposed within a second balloon, each balloon defining a chamber and having a proximal neck coupled to the distal portion of catheter body to form a proximal seal, and each balloon having a distal neck coupled to the distal portion of the shaft, the distal neck of the second balloon forming a distal seal that is substantially coterminous with the distal portion of the shaft;
    a fluid injection conduit disposed within the chamber of the first balloon;
    the first balloon being symmetrically positioned within the second balloon, with the proximal seal of the first balloon comprising an adhesive junction between the first balloon and the distal portion of the catheter body and extending within the chamber of the first balloon, and the proximal seal of the second balloon comprising an adhesive junction between the second balloon and the distal portion of the catheter body at a distance proximal to the proximal seal of the first balloon, the proximal seal of the second balloon extending externally to the chamber of the first balloon;
    the distal seal of the first balloon comprising an adhesive junction between the first balloon and the distal portion of the shaft, the first balloon having an outer surface and an inner surface, the distal seal of the first balloon extending within the chamber of the first balloon between the outer surface of the first balloon and the shaft;
    the second balloon defining a distal face when inflated, the shaft being coterminous with the distal face; and
    the proximal seal and the distal seal of the first balloon each defining a length of approximately 10% to 30% of the inflated balloon length.

* * * * *